(12) United States Patent
Nakamura

(10) Patent No.: US 10,288,859 B2
(45) Date of Patent: May 14, 2019

(54) SURGICAL MICROSCOPE SYSTEM

(71) Applicant: MITAKA KOHKI CO., LTD., Tokyo (JP)

(72) Inventor: Katsuyuki Nakamura, Tokyo (JP)

(73) Assignee: MITAKA KOHKI CO., LTD., Tokyo (JP)

( * ) Notice: Subject to any disclaimer, the term of this patent is extended or adjusted under 35 U.S.C. 154(b) by 0 days.

(21) Appl. No.: 15/669,078

(22) Filed: Aug. 4, 2017

(65) Prior Publication Data
US 2018/0045936 A1 Feb. 15, 2018

(30) Foreign Application Priority Data
Aug. 15, 2016 (JP) .................. 2016-159200

(51) Int. Cl.
| | |
|---|---|
| G02B 21/00 | (2006.01) |
| A61B 90/25 | (2016.01) |
| A61B 90/50 | (2016.01) |
| G02B 21/02 | (2006.01) |
| G02B 21/22 | (2006.01) |
| A61B 90/20 | (2016.01) |

(52) U.S. Cl.
CPC .......... *G02B 21/0012* (2013.01); *A61B 90/20* (2016.02); *A61B 90/25* (2016.02); *A61B 90/50* (2016.02); *G02B 21/025* (2013.01); *G02B 21/22* (2013.01)

(58) Field of Classification Search
CPC .. G02B 21/0012; G02B 21/025; G02B 21/22; A61B 90/50; A61B 90/25; A47F 5/00
USPC ................. 359/374–378; 248/123.2
See application file for complete search history.

(56) References Cited

U.S. PATENT DOCUMENTS

| | | | |
|---|---|---|---|
| 5,528,417 A | 6/1996 | Nakamura | |
| 7,088,504 B2 | 8/2006 | Fukaya et al. | |
| 8,416,492 B2 | 4/2013 | Enge | |
| 2001/0010592 A1* | 8/2001 | Nakamura | G02B 21/22 359/376 |
| 2004/0120031 A1 | 6/2004 | Fukaya et al. | |
| 2004/0120032 A1* | 6/2004 | Sander | G02B 21/22 359/376 |
| 2004/0136059 A1* | 7/2004 | Sander | G02B 21/22 359/378 |
| 2004/0184141 A1* | 9/2004 | Sander | G02B 21/22 359/368 |
| 2004/0252371 A1* | 12/2004 | Sturgis | G02B 21/18 359/368 |

(Continued)

FOREIGN PATENT DOCUMENTS

| | | |
|---|---|---|
| JP | 2825721 | 11/1998 |
| JP | 2003-202504 | 7/2003 |

(Continued)

OTHER PUBLICATIONS

Office Action issued in Japan Counterpart Patent Appl. No. 2016-159200, dated Jul. 25, 2017, along with a partial english translation thereof.

*Primary Examiner* — Frank G Font
(74) *Attorney, Agent, or Firm* — Greenblum & Bernstein, P.L.C.

(57) ABSTRACT

A surgical microscope has an upper face provided with a light beam outlet. An assistant scope is mounted on the light beam outlet, and is rotatable in a horizontal plane so as to direct in any direction in the plane.

2 Claims, 7 Drawing Sheets

(56) References Cited

U.S. PATENT DOCUMENTS

| | | | | |
|---|---|---|---|---|
| 2005/0247831 | A1* | 11/2005 | Nakamura | F16M 11/105 248/123.2 |
| 2006/0215258 | A1* | 9/2006 | Strobel | G02B 21/22 359/368 |
| 2008/0100893 | A1* | 5/2008 | Knuenz | G02B 21/22 359/196.1 |
| 2008/0231948 | A1* | 9/2008 | Nakamura | A61B 90/36 359/378 |
| 2008/0239473 | A1* | 10/2008 | Takagi | G02B 21/0012 359/368 |
| 2009/0116102 | A1* | 5/2009 | Higuchi | G02B 21/0012 359/377 |
| 2009/0190209 | A1* | 7/2009 | Nakamura | G02B 21/0012 359/375 |
| 2009/0219613 | A1 | 9/2009 | Enge | |
| 2009/0268281 | A1* | 10/2009 | Schnitzler | G02B 21/22 359/377 |
| 2011/0134518 | A1* | 6/2011 | Doi | A61B 19/5223 359/384 |
| 2014/0139916 | A1* | 5/2014 | Doi | G02B 21/0012 359/477 |
| 2014/0211304 | A1* | 7/2014 | Nakamura | G02B 21/22 359/363 |
| 2015/0301326 | A1* | 10/2015 | Doi | G02B 21/362 348/45 |
| 2017/0020624 | A1* | 1/2017 | Guentert | A61B 90/25 |

FOREIGN PATENT DOCUMENTS

| | | |
|---|---|---|
| JP | 2005-137577 | 6/2005 |
| JP | 2009-201996 | 9/2009 |

* cited by examiner

SURGICAL MICROSCOPE SYSTEM

CROSS-REFERENCE TO RELATED APPLICATIONS

This application claims priorities from Japanese Patent Application No. 2016-159200 filed on Aug. 15, 2016; the entire contents of which are incorporated herein by reference.

BACKGROUND

1. Technical Field

The present disclosure relates to surgical microscope systems in which a side face of a surgical microscope is supported to a tip of a stand via a longitudinal slider and a lateral slider.

2. Description of the Related Art

A surgical microscope has been used in neurosurgery and the like. When the surgical microscope is used, it is hung and supported by a stand. The stand includes a supporting arm laterally extending. The supporting arm is provided with a hanging arm longitudinally extending downward from a tip of the supporting arm. The surgical microscope is supported to a lower end of the hanging arm. A longitudinal slider and a lateral slider are installed on a side face of the surgical microscope. Aforementioned two sliders are mutually stacked to form a cross or the like. The surgical microscope is supported to the lower end of the hanging arm via the two sliders without being rotated around a pivot as a rotation axis.

In the above configuration, the surgical microscope can move in vertical and horizontal directions with respect to the lower end of the hanging arm, and the weight balance is equalized (balanced) around the pivot at the lower end of the hanging arm. Accordingly, even when the surgical microscope is released from someone's hand at some rotational position, it can stay at the rotational position while the attitude is maintained (see Japanese Patent No. 2825721).

A light beam outlet is formed in a side face of the surgical microscope opposite to a side face on which the longitudinal slider and lateral slider is installed. An assistant scope is detachably mounted to the light beam outlet. An assistant of a surgeon can observe the same surgical field which the surgeon observes using the surgical microscope, thereby assisting an operation by the surgeon.

SUMMARY

In the conventional apparatus as described above, an adjustment of the weight balance around a rotation axis of the surgical microscope is carried out in advance. However, since the longitudinal and lateral sliders forms a cross or the like and are positioned at a side face of the surgical microscope near which the hanging arm exists, these sliders interfere with forming the light beam outlet at the side face. This means that it is impossible to attach the assistant scope to the side face. Since the assistant scope can be attached only to another side face near which the hanging arm does not exist, the assistant is forced to stand at a position where the hanging arm is not positioned, and is also forced to observe a surgical field from the position.

The present disclosure is intended for providing a surgical microscope system which enables an assistant to stand at any positions in addition to a position where a hanging arm does not exist, around a surgical microscope and to observe therefrom through an assistant scope.

An aspect of the present disclosure is a surgical microscope system comprising: a stand provided with a first arm and a second arm, the first arm laterally extending, and the second arm extending downward from a tip of the first arm and including a pivot at a lower end of the second arm; longitudinal and lateral sliders; a surgical microscope having a side face supported by the pivot via the longitudinal and lateral sliders, the surgical microscope including: an objective lens system vertically arranged; a zoom lens system horizontally arranged; a first reflector configured to horizontally reflect a pair of light beams from a surgical field through the objective lens system to arrange the light beams left and right; a pair of second reflectors arranged below and above configured to reversely reflect the light beams from the zoom lens system above the zoom lens system to guide the light beams to an eyepiece unit; a beam splitter configured to upward split a part of one of the light beams reversely reflected; a light beam outlet provided above the beam splitter to extract light beam split by the beam splitter; a rotary barrel mounted on the light beam outlet, the rotary barrel being rotatable in a horizontal plane and including a third reflector configured to horizontally reflect the split light beam; and an assistant scope detachably attached to the rotary barrel.

The beam splitter may be provided in an optical path of the light beam close to the hanging arm.

According to the present disclosure, it is possible to provide a surgical microscope system which enables an assistant to stand at any positions in addition to a position where a hanging arm does not exist, around a surgical microscope and to observe therefrom through an assistant scope.

DESCRIPTION OF THE EMBODIMENTS

Figure 1:
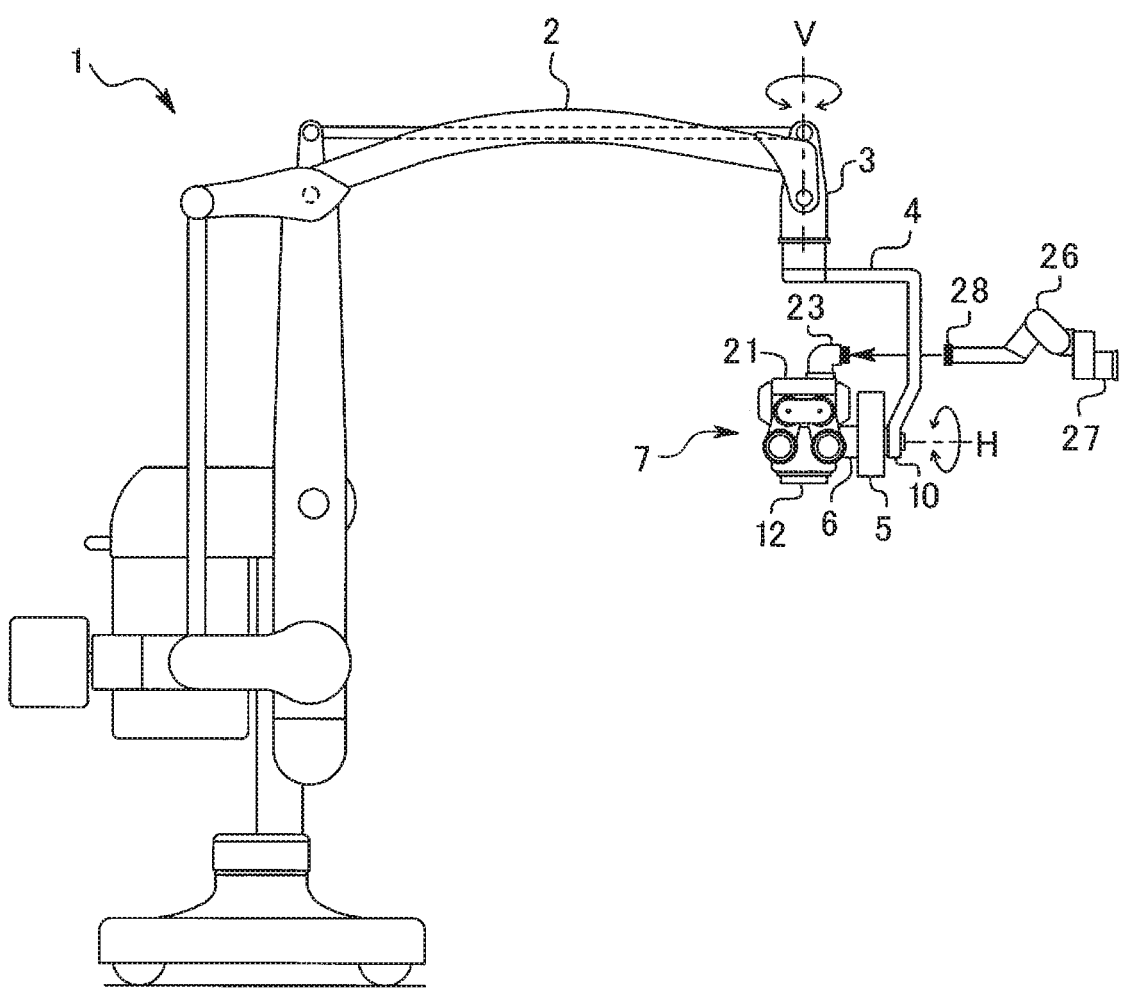
FIG. 1 is a side view of a surgical microscope system supported by a stand.
Figure 2:
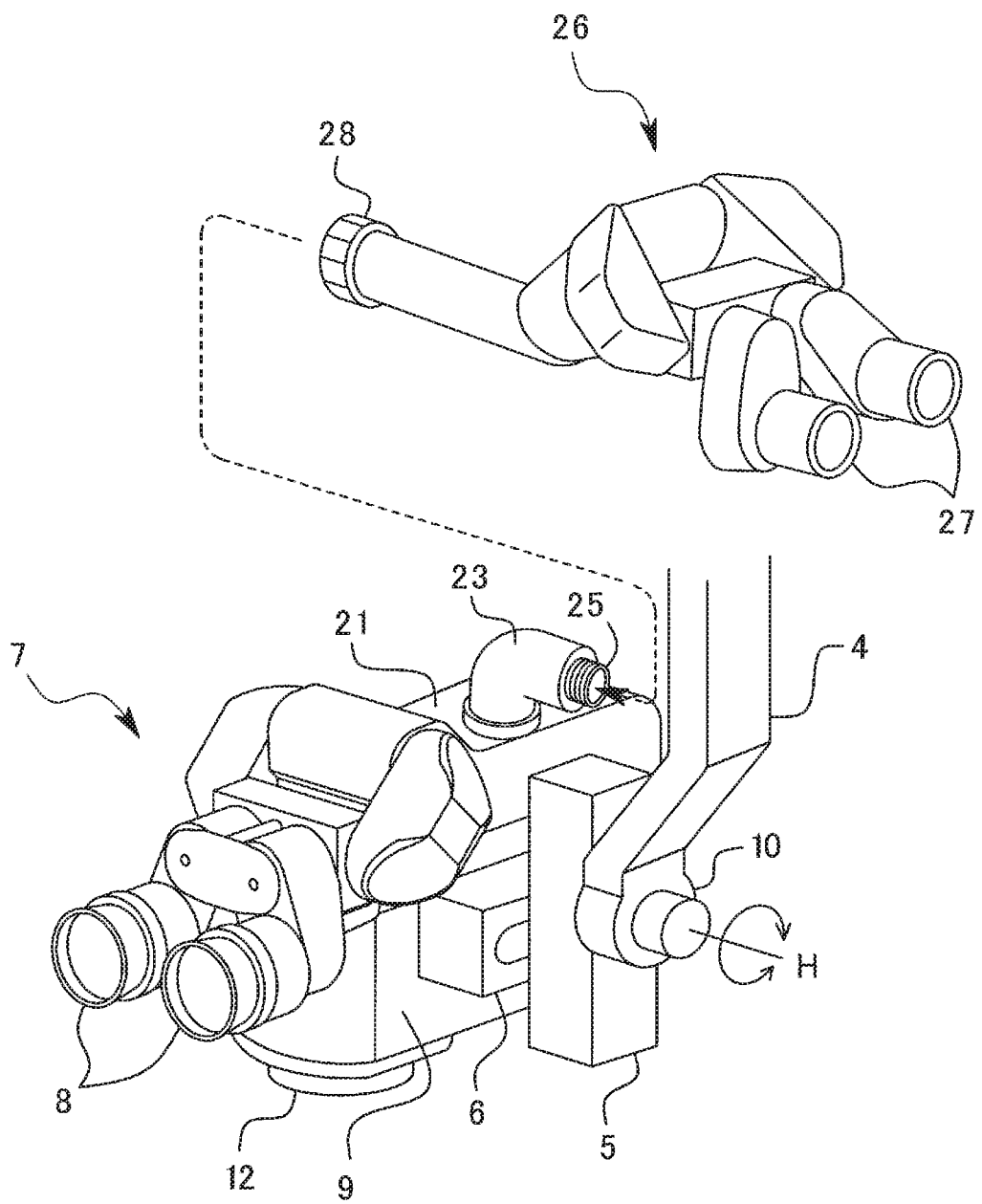
FIG. 2 is a perspective view of a surgical microscope and an assistant scope.
Figure 3:
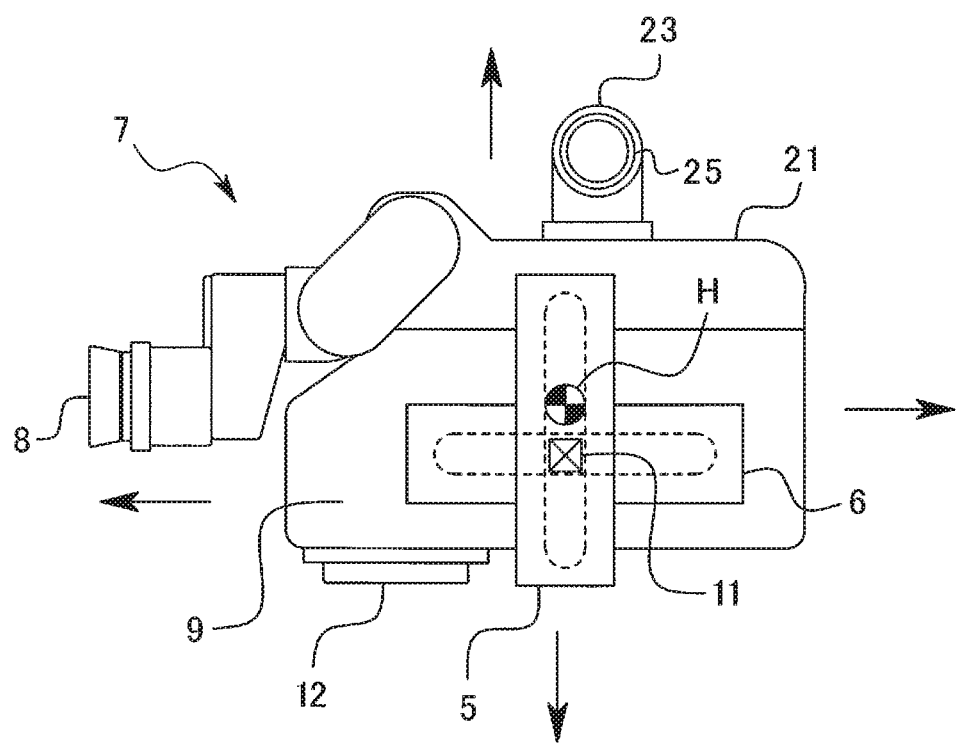
FIG. 3 is a side view of a longitudinal slider and a lateral slider, for the surgical microscope.

An embodiment according to the present disclosure will be described hereinafter. In the description as described above and below, a term "front" means an eyepiece side of a surgical microscope, a term "rear" means an opposite side of the eyepiece side in the surgical microscope. Further, terms "left" and "right" mean directions when viewed the surgical microscope from the eyepiece side.

Firstly, a stand 1 will be described. The stand 1 includes a supporting arm (first arm) 2 on an upper portion of the stand 1. The supporting arm 1 is integrally formed with the stand 1, and extends laterally. A tip link 3 vertically extending is attached to a tip end of the supporting arm 2. A hanging arm (second arm) 4 is provided at a lower end of the tip link 3. The hanging arm 4 is rotatable in a horizontal plane (horizontal direction) around a vertical shaft V as a rotation center.

A surgical microscope 7 is supported at a lower end 10 of the hanging arm 4 via a longitudinal slider (vertical slider) 5 and a lateral slider (horizontal slider) 6. The surgical microscope 7 includes an eyepiece unit 8 on the front side thereof. The lateral slider 6 is fixed to a right side 9 of the surgical microscope 7. The longitudinal slider 5 is mounted on the lateral slider 6 to form in a cross or the like together with the lateral slider 6.

The lower end 10 of the hanging arm 4 is pivotally supported to a center of the longitudinal slider 5. With this, the surgical microscope 7 can rotate around a pivot horizontally provided as a rotation axis. The rotation of the pivot H is stopped and released by a clutch (not shown).

The surgical microscope 7 must not rotate arbitrarily even when the pivot H is free by the release of the clutch. Nevertheless, a surgeon can manipulate the surgical microscope 7 to freely rotate around the pivot H. In this regard, if a weight of the surgical microscope is not balanced, the surgical microscope 7 comes to arbitrarily rotate and it becomes hard to manipulate the surgical microscope 7.

Aforementioned longitudinal slider 5 and lateral slider 6 are provided to adjust the weight balance around the pivot H. Both sliders 5 and 6 are coupled with each other by a top 11 formed in a nut-like shape. In the top 11, threaded rods (not shown) respectively installed in the longitudinal slider 5 and the lateral slider 6 are screwed. Respective threaded rods can be turned in any of a forward direction and reverse direction by a motor (not shown) which is controlled by a switching unit (not shown). With the rotations of respective threaded rods, a position of the surgical microscope 7 can be slid forward, backward, upward and downward with respect to the lower end 10 of the hanging arm 4 (i.e. pivot H). With aforementioned slides, the center of gravity of the surgical microscope 7 comes to coincide with the position of the pivot H, thereby the weight of the surgical microscope 7 is balanced around the pivot 7.

Next, a structure of the surgical microscope 7 will be described.

The surgical microscope 7 has a configuration which enables a stereoscopic observation. Left and right light beams (a pair of light beams) 'A' from a surgical field as an observation object are guided to the inside of the surgical microscope 7 through a light beam inlet 12. Several lenses as an objective lens system 13 are vertically arranged above the light beam inlet 12. Prisms 14 as a first reflector (reflective means) is located above the objective lens system 13. The prisms 14 horizontally reflect the light beams passing through the objective lens system 13. Several lenses as a zoom lens system 15 are horizontally arranged behind the prisms 14.

Two prisms 16 and two prisms 17 as a pair of second reflectors (reflective means) are provided below and above, behind the zoom lens system 15. After the light beams 'A' passes through the zoom lens system 15, they are reflected upward by the prisms 16 and reflected forward above the zoom lens system 15 by the prisms 17. That is, the prisms 16 and 17 reversely reflect the light beams 'A'. The light beams 'A' thus reflected forward passes through an imaging lens 18. Thereafter, the light beams 'A' are guided to an eyepiece unit 8 including eyepieces, thereby the surgeon carried out a stereoscopic observation from the eyepiece unit 8.

A beam splitter 20 as a light splitting means is arranged in an optical path of the right one of the light beams 'A' that have been reversely reflected above the zoom lens system 15. Here, the right light beam is located closer to the hanging arm than the left light beam. Specifically, the beam splitter 20 is provided in an optical path of the light bean close to the hanging arm 4. A part of the right light beam 'A' is split upward as a light beam B.

Figure 7:
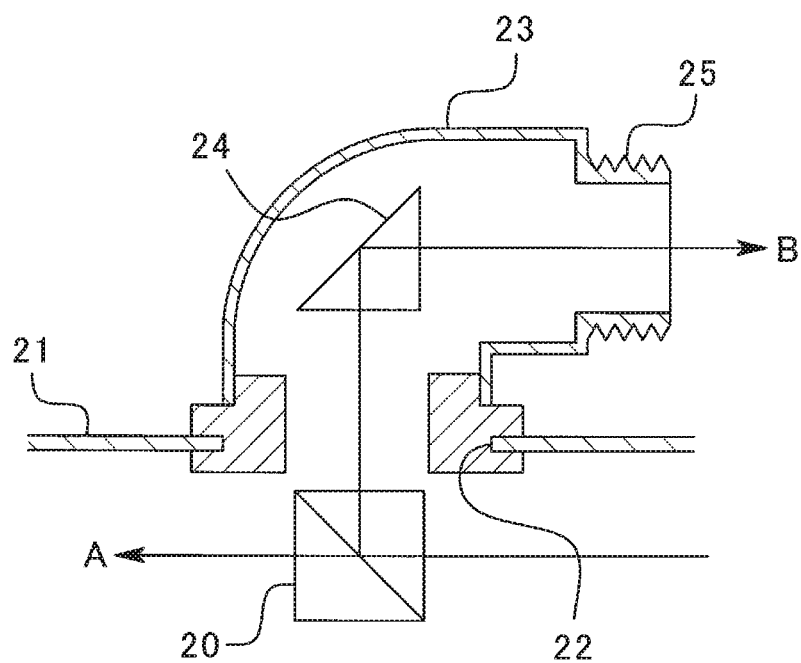
FIG. 7 is a sectional view of a light beam outlet.

A light beam outlet (light beam extraction port) 22 (see FIG. 7) is formed in an upper face of the surgical microscope 7, which corresponds to an upper part of the beam splitter 20. Since the beam splitter 20 is located on the right side, the light beam outlet 22 is located on a right side of the upper face 21 of the surgical microscope 7. A rotary barrel 23 is mounted on the light beam outlet 22. The rotary barrel 23 is bent at right angles, and is rotatable in a horizontal plane. The rotary barrel 23 is provided with a prism 24 as a third reflector (reflective means) installed therein. The prism 24 horizontally reflects the light beam B vertically passing. A tip of the rotary barrel 23 includes a screwed portion 25 forming a male screw.

An assistant scope 26 includes a binocular eyepiece section 27 and a tip provided with a cup 28. The cup 28 has an inner surface forming a female screw. The tip of the assistant scope 26 is inserted into the tip of the rotary barrel 23 and the cup 28 is screwed in the screwed portion 25. With this operation, the assistant scope 26 can be attached to the rotary barrel 23.

When the assistant scope 26 is connected with the rotary barrel 23, the light beam B is guided to the inside of the assistant scope 26. Accordingly, using the assistant scope, an assistant can observe the same image of the surgical field G, which the surgeon observes with the eyepiece unit 8 of the surgical microscope 7.

Figure 4:
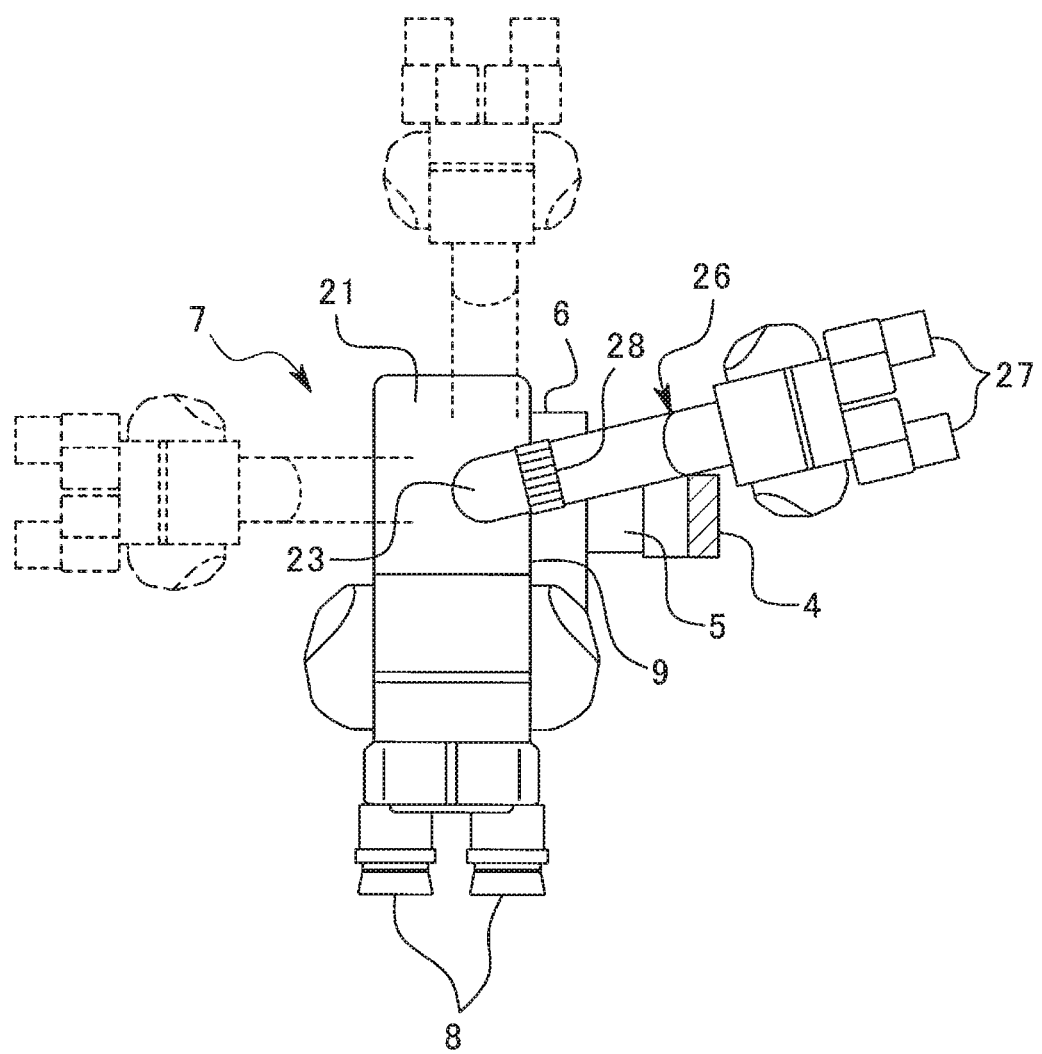
FIG. 4 is a plan view of the surgical microscope and the assistant scope.
Figure 5:
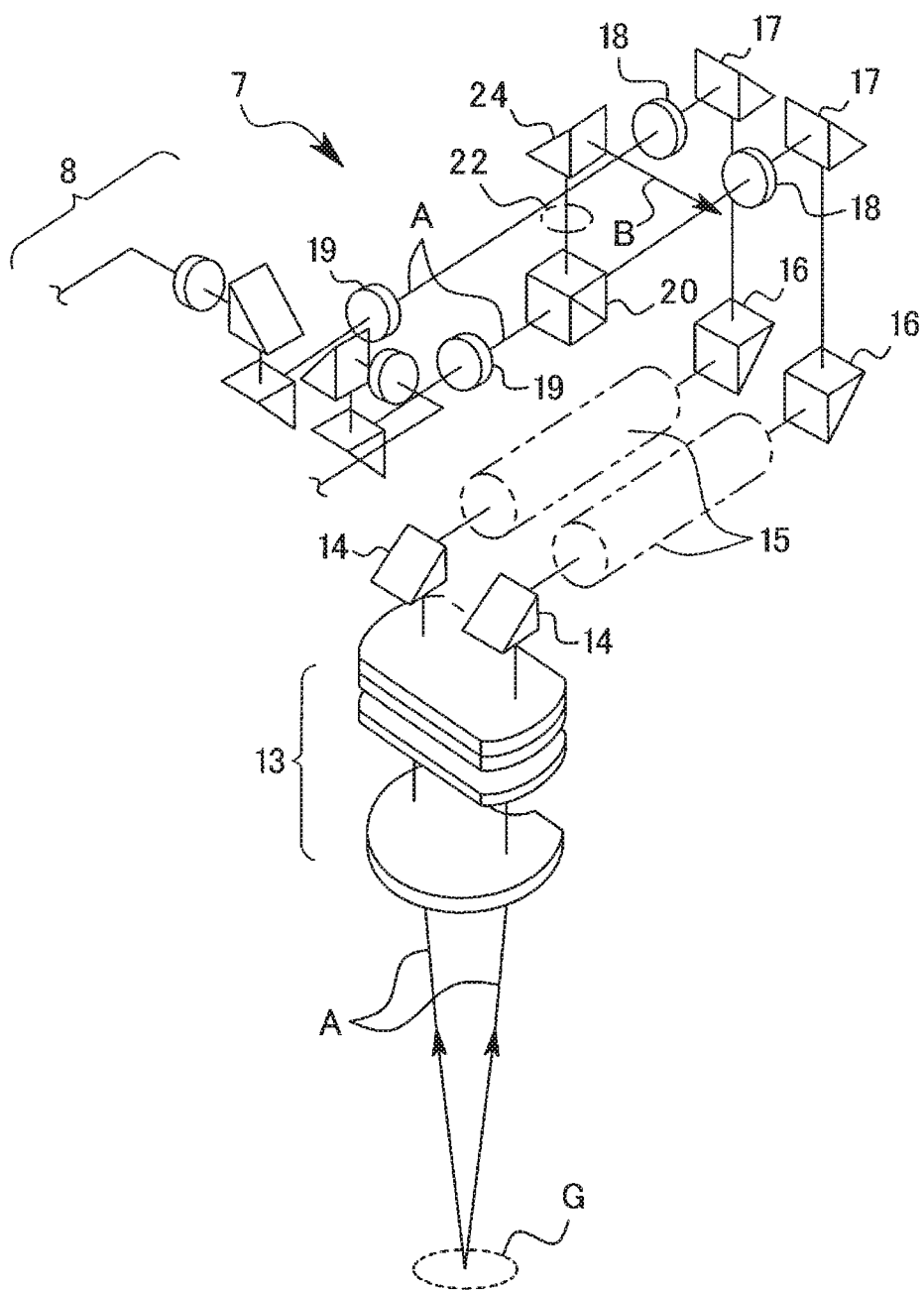
FIG. 5 is a perspective view of an optical configuration in the surgical microscope.
Figure 6:
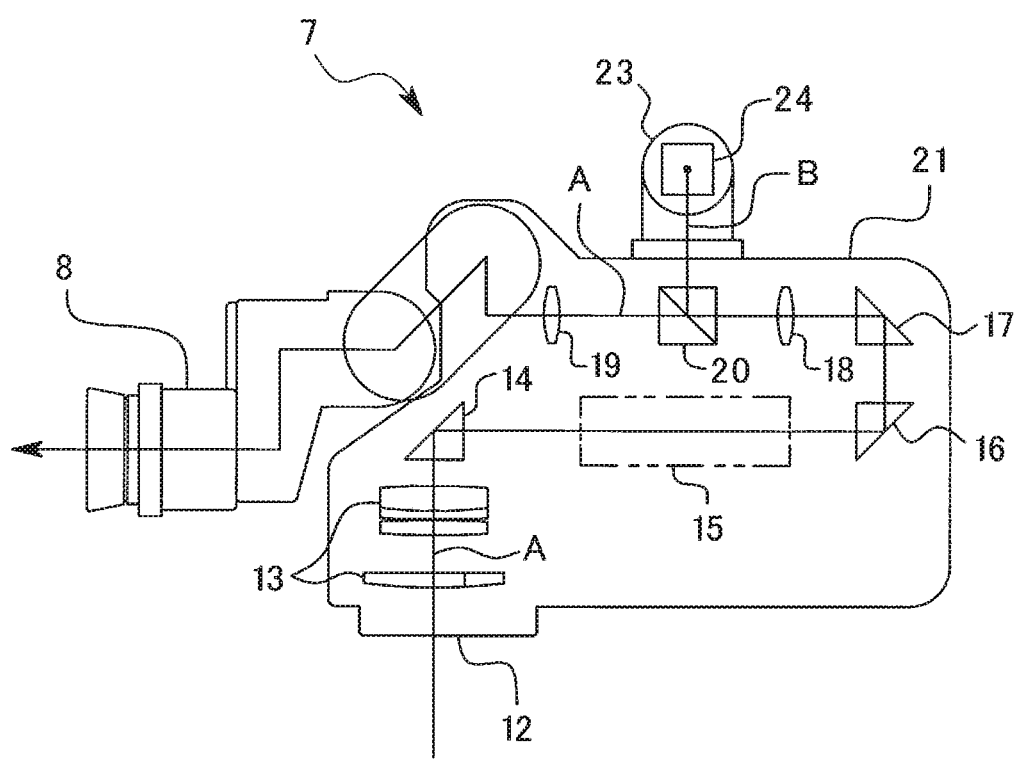
FIG. 6 is a side view of the optical configuration in the surgical microscope.

The assistant scope becomes rotatable in the horizontal plane around the rotary barrel 23 as a rotation center by connecting the assistant scope 26 with the rotary barrel 23. As shown in FIG. 4, the assistant scope 26 can freely rotate to the left side and the back side of the surgical microscope 7, where the hanging arm 4 does not exist. Further, the assistant scope 26 can also rotate even to the right side of the surgical microscope 7 where the hanging arm 4 exists, except of a slight range in which the assistant scope 26 interferes with the hanging arm 4. The assistant scope 26 is not required to rotate to the front side of the surgical microscope 7 because the surgeon is supposed to stand on the front side of the surgical microscope 7.

A position of the hanging arm 4 in a front-back direction with respect to the lateral slider 6 varies in an initial adjustment of the balance. Accordingly, a direction of assistant scope 26 when contacting with the hanging arm 4 varies depending on the position of the hanging arm 4.

If the hanging arm 4 is positioned relatively on the front side, the assistant scope 26 can completely turn in the right direction. On the other hand, if the hanging arm 4 is positioned relatively on the rear side, the assistant scope 26 directs in a direction, which is inclined slightly backward to the right direction, while being contact with the hanging arm 4 (see FIG. 4).

Nevertheless, the assistant scope 26 has a length which positions whole of the eyepiece unit 27 further on the right side than the hanging arm when the assistant scope 26 contacts with the hanging arm 4. Accordingly, even when the assistant scope 26 turns in the right direction, the hanging arm 4 does not interfere with the observation by the assistant scope 26. As described above, the rotary barrel 23 is positioned in a right region of the upper face 21 of the surgical microscope 7 and the assistant scope 26 extends from the rotary barrel 23. Accordingly, the assistant scope 26 is likely to be positioned further on the right side than the hanging arm 4, and thus it is possible to reduce the length of the assistant scope 26.

In other words, if the rotary barrel would be positioned in a left region of the upper face 21, the assistant scope 26 would be required to have a length which projects the eyepiece unit 27 further to the right side than the hanging arm 4. In this case, the length of the assistant scope 26 should be relatively long. In contrast, the present embodiment does not require such length of the assistant scope 26. If a reduction of the length of the assistant scope 26 can avoid an extreme (unnecessary) projection itself and can provide an easy observation, for example, when the assistant scope 26 turns to the left or rear.

In the present embodiment, only one of the light beam (i.e. only the right light beam 'A') is branched by the beam splitter 20, and one of the branched light beam travels upward as the light beam B. Accordingly, an optical system in the rotary barrel 23 becomes simpler than an optical system for a stereoscopic observation. That is, an optical system installed in the rotary barrel 23 can be configured only with the prism 24 which guides the light beam B to the assistant scope 26.

According to the present embodiment, the assistant scope 26 is rotatably provided on the upper face 21 of the surgical microscope 7. Therefore, it is possible to freely change the direction of the assistant 26 except of the slight range in which the assistant scope 26 interferes with the hanging arm 4. Accordingly, the assistant can observe the surgical field G using the assistant scope 26 at any standing positions around the surgical microscope 7 to assist a surgery.

What is claimed is:

1. A surgical microscope system comprising:
   a stand provided with a first arm and a second arm, the first arm laterally extending from the stand, and the second arm extending downward from a tip end of the first arm and including a pivot at a lower end of the second arm;
   longitudinal and lateral sliders;
   a surgical microscope having a side face supported by the pivot via the longitudinal and lateral sliders, the surgical microscope including:
   an objective lens system vertically arranged;
   a zoom lens system horizontally arranged;
   a first reflector provided between the objective lens system and the zoom lens system and configured to horizontally reflect a pair of light beams passing from the objective lens system such that the light beams are arranged in two parallel first optical paths extending in a horizontal direction of the surgical microscope;
   a pair of second reflectors provided rearwardly of the zoom lens system and configured to reversely reflect the light beams passing from the zoom lens system in two parallel second optical paths extending in the horizontal direction above the zoom lens system to guide the light beams to an eyepiece unit;
   a beam splitter configured to split a part of one of the light beams reversely reflected by the pair of second reflectors such that the part of the one of the light beams is reflected upwards;
   a light beam outlet provided above the beam splitter to extract the part of the one of the light beams split upward by the beam splitter;
   a rotary barrel mounted on the light beam outlet, the rotary barrel being rotatable in a horizontal plane and including a third reflector configured to horizontally reflect the part of the one of the light beams split upwards by the beam splitter; and
   an assistant scope detachably attached to the rotary barrel.

2. The surgical microscope system according to claim 1, wherein
   the beam splitter is provided in one of the two parallel second optical paths that is closest to the second arm.

\* \* \* \* \*